US006583117B2

(12) United States Patent
Owen et al.

(10) Patent No.: US 6,583,117 B2
(45) Date of Patent: Jun. 24, 2003

(54) METHOD OF TISSUE REPAIR

(75) Inventors: Earl Ronald Owen, Sydney (AU);
Rodney Ian Trickett, Sydney (AU);
Antonio Lauto, Sydney (AU); Judith Margaret Dawes, Sydney (AU); James Austin Piper, Sydney (AU)

(73) Assignees: The Microsearch Foundation of Australia, New South Wales (AU);
Macquarie Research Ltd., New South Wales (AU)

( * ) Notice: Subject to any disclaimer, the term of this patent is extended or adjusted under 35 U.S.C. 154(b) by 0 days.

(21) Appl. No.: 09/769,585

(22) Filed: Jan. 25, 2001

(65) Prior Publication Data
US 2002/0045732 A1 Apr. 18, 2002

Related U.S. Application Data

(62) Division of application No. 08/875,228, filed as application No. PCT/AU96/00024 on Jan. 19, 1996, now Pat. No. 6,211,335.

(30) Foreign Application Priority Data

Jan. 20, 1995 (AU) .............................................. PN0667

(51) Int. Cl.⁷ .............................................. A61K 38/00
(52) U.S. Cl. .............................. 514/12; 514/21; 606/2; 606/8; 606/213; 606/214
(58) Field of Search .......................... 514/12, 21; 606/2, 606/8, 213, 214

(56) References Cited

U.S. PATENT DOCUMENTS

| | | |
|---|---|---|
| 4,493,320 A | 1/1985 | Treat |
| 4,672,969 A | 6/1987 | Dew |
| 4,725,671 A | 2/1988 | Chu |

(List continued on next page.)

FOREIGN PATENT DOCUMENTS

| | | |
|---|---|---|
| WO | WO91/04073 A1 | 4/1991 |
| WO | WO92/14513 A1 | 9/1992 |
| WO | WO94/21306 A1 | 9/1994 |
| WO | WO96/03159 A1 | 2/1996 |

OTHER PUBLICATIONS

Dix Poppas et al, "Preparation of Human Albumin Solder for Laser Tissue Welding", Lasers in Surgery and Medicine, 13:577–580 (1993).

Dix Poppas et al, "Laser Welding in Urethral Surgery: Improved Results with a Protein Solder", Journal of Urology, 139:415–417 (Feb., 1988).

R. Malik et al, "A New Method for Recording and Analysing Evoked Motor Potentials from Dogs", Journal of Small Animal Practice, 30:13–19 (1989).

R. Malik et al, "Motor Nerve Conduction Parameters in the Cat", Journal of Small Animal Practice, 30:396–400 (1989).

Antonio Lauto et al, "Laser Activated Protein Bands for Peripheral Nerve Repair", SPIE, 2623:416–425 (1987).

Michael Treat et al, "New Technologies and Future Applications of Surgical Lasers", Lasers in General Surgery, 72(3):705–742 (Jun., 1992).

Thomas Menovsky et al, "$CO_2$ Laser Nerve Welding: Optimal Laser Parameters and the Use of Solders in Vitro", Microsurgery, 15:44–51 (1994).

(List continued on next page.)

Primary Examiner—Raymond Henley, III
Assistant Examiner—C. Delacroix-Muirheid
(74) Attorney, Agent, or Firm—Howson and Howson

(57) ABSTRACT

A method for joining tissue comprising aligning and abutting edges of the tissue to be joined applying a biodegradable, biological solder or an analogue thereof, across the edges and exposing the solder to an energy source under conditions which provide transfer of energy from the source to the solder to cause the solder to bond to the tissue surface adjacent the edges to provide a weld holding the edges together.

50 Claims, 12 Drawing Sheets

U.S. PATENT DOCUMENTS

| | | |
|---|---|---|
| 4,854,320 A | 8/1989 | Dew |
| 4,973,466 A | 11/1990 | Reich |
| 5,002,051 A | 3/1991 | Dew |
| 5,071,417 A | 12/1991 | Sinofsky |
| 5,140,984 A | 8/1992 | Dew |
| 5,156,613 A | 10/1992 | Sawyer |
| 5,209,776 A | 5/1993 | Bass |
| 5,254,113 A | 10/1993 | Wilk |
| 5,292,253 A | 3/1994 | Levy |
| 5,292,362 A | 3/1994 | Bass |
| 5,330,974 A | 7/1994 | Pines |
| 5,334,191 A | 8/1994 | Poppas |
| 5,409,479 A | 4/1995 | Dew et al. |
| 5,409,481 A | 4/1995 | Poppas |
| 5,552,452 A | 9/1996 | Khadem |
| 5,556,414 A | 9/1996 | Turi |
| 5,571,216 A | 11/1996 | Anderson |
| 5,611,794 A | 3/1997 | Sauer |
| 5,662,643 A | 9/1997 | Kung |
| 5,662,712 A | 9/1997 | Pathak |
| 5,669,934 A | 9/1997 | Sawyer |
| 5,713,891 A | 2/1998 | Poppas |
| 5,749,895 A | 5/1998 | Sawyer |
| 6,211,335 B1 * | 4/2001 | Owen et al. ................ 530/350 |

OTHER PUBLICATIONS

R. Chuck et al, "Dye-enhanced Laser Tissue Welding", Lasers Surg. Med., 9(5):471–477 (1989) (NCBI PubMed PMID:2478852, UI:90042964—Abstract only).

S. Libutti et al, "Canine Colonic Anastomoses Reinforced with Dye-enhanced Fibrinogen and a Diode Laser", Surg. Endosc., 4(2):97–99 (1990) (NCBI PubMed PMID:2374989, UI:90327231—Abstract only).

N. Moazami et al, "Reinforcement of Colonic Anastomoses with a Laser and Dye-enhanced Fibrinogen", Arch. Surg., 125(11):1452–1454 (Nov., 1990) (NCBI PubMed PMID:2241556, UI:91053730—Abstract only).

R. White et al, "Comparison of Laser-welded and Sutured Arteriotomies", Arch. Surg., 121(10):1133–1135 (Oct., 1986) (NCBI PubMed PMID:3533008, UI:87025116—Abstract only).

R. White et al, "Argon Laser-welded Arteriovenous Anastomoses", J. Vasc. Surg., 6(5):447–453 (Nov., 1987) (NCBI PubMed PMID:3312648, UI:88036297—Abstract only).

* cited by examiner

METHOD OF TISSUE REPAIR

CROSS REFERENCE TO RELATED APPLICATION

This is a divisional of U.S. patent application Ser. No. 08/875,228, filed Oct. 17, 1997, now U.S. Pat. 6,211,335, which is a §371 of PCT/AU96/00024, filed Jan. 19, 1996.

TECHNICAL FIELD

The present invention relates to methods for joining living tissues, including veins, arteries, microvessels, tubes, nerves, organ tissues and biological surfaces, such as peritoneum, omentum, fascia, shin, artificial tissues, and to pharmaceutical products useful in joining these tissues.

BACKGROUND ART

Joining tissues such as veins, arteries, microvessels, tubes, nerves, tissues and biological surfaces such as the peritoneum and skin has mainly been carried out clinically to date by suturing and microsuturing.

Microsuturing requires considerable skill and is a time consuming procedure. Frequently, tissues which have been joined by microsuturing form considerable scar tissue. Some of the difficulties encountered with microsuturing can be better understood by considering the example of rejoining damaged peripheral nerve tissue.

Peripheral Nerves

The electrical signals that control the body's organs and transmit information back and forth to the central nervous system (CNS) travel along peripheral nerves. The structure of these peripheral nerves is analogous to telephone cables. In a telephone cable there is a strong protective outer coating that protects all the inner components. The copper wires are often grouped in separate insulating tubes that lead to different systems. Each of the inner copper wires is a single line that can transmit electricity in either direction and has an insulating coating around it so that it does not interfere with the lines next to it.

A peripheral nerve (FIG. 1) has an outer membrane consisting of connective tissue such as collagen. This membrane (epineurium) protects and holds the separate nerve bundles together. The nerve bundles which lie inside this membrane are called fascicles. These fascicles also have a collagen based surrounding membrane and their task is to group together nerve axons supplying a similar area of the body. Inside the fascicle membrane the axons are surrounded by loose connective tissue. The axons are a long extension from a cell body which is contained within the CNS in the spine or the brain. Sensory axons transmit to the CNS and motor axons transmit from the CNS. Nerve metabolism is sustained by the vascular system from both outside the nerve and along the centre of the nerve.

Peripheral nerves can have very small diameters. For instance, the mature median nerve at the wrist is approximately 1 cm in diameter and contains an average of forty fascicles, each of which can contain up to 4500 axons. When a peripheral nerve is cut all axons distal to the wound change their properties as axon flow is cut off from the cell body. Even when the nerve is reconnected, these axons continue to degenerate distally. The Schwann cells which normally wrap themselves around the axons as insulation guide regenerating axons. Joining nerves as accurately as possible by lining up corresponding fascicles enables the axons to more efficiently regenerate.

Operating upon nerves has been facilitated by using magnification and special microsurgical equipment. Accurate repairs need to be effected at the fascicular level ensuring that regeneration is along the correct bundle leading to the original area those axons supplied. The current technique of peripheral nerve repair uses microsuturing (FIG. 2). This technique requires a dedicated, trained surgeon as microsuturing of just one of the many fascicles with three or more microsutures (using say a 70 micron diameter needle and 30 micron thread) can take very long operating times.

Microsuturing is at present clinically used where the skills are available. Unfortunately, there are relatively few surgeons who have the necessary manipulative skills for operating at high magnification. Even a reasonable microsuturing technique results in long operating times with added damage to the inner axons due to sutures penetrating the thin insulating perineurial sheath. The use of sutures results in some scarring of the repair due to foreign body reaction. There is also evidence which indicates that in the long term scar tissue formation and scar maturation can lead to impairment of the joined nerve.

Work has been performed on the use of lasers alone in effecting nerve joins. One of the problems of laser welding has been the fact that the intact gel-like nerve tissue of the axons is actually under pressure within the fascicle. When the fascicle is cut this material extrudes. This can lead to the direct laser weld being formed on nerve tissue rather than the surrounding membrane of the fascicle, causing nerve damage. To date the welds have typically been made using infrared lasers such as $CO_2$ lasers which rely on water absorption for energy transfer. Tissue preparation before welding relies on overlapping the nerve membranes. This is difficult due to the extruding gel-like axons and so can lead to denaturation of the nerve axon material. The affected tissue tends to scar and the fibrous tissue that proliferates as a result is a poorer electrical conductor than nerve tissue. The bonds formed to date as described in the prior art using laser welding have typically lacked strength. These laser joins alone tend to fail so microsuturing has been used in addition to welding to strengthen these joins.

To deal with at least some of the deficiencies of laser welding, various glues have been used in forming the welds. These low protein concentration, fluid glues tend to run between the ends of the nerve that are being joined which may result in damage to the axoplasm of the nerve fascicle and also hinder regeneration. They are also applied around the join which is then circumferentially welded. These joins later show thick scarring which causes stricture of the nerve. Moreover, the joins tend to be weak.

The welding techniques so far available also tend to lack precision. Factors that influence the precision of this approach adversely include differences in: the consistency of the glue used; the aperture of the needle or other device used to apply the glue; and the pressure exerted in applying the glue.

DESCRIPTION OF THE INVENTION

The present invention provides a method for joining tissue comprising:

aligning and abutting edges of the tissue to be joined;

applying a solder, across the aligned and abutted edges; and exposing the solder to an energy source under conditions which provide a transfer of energy from the source to the solder to cause the solder to bond to the tissue surface adjacent the edges thus providing a weld holding the edges together.

In addition to causing the solder to bond to the protein of the underlying tissue, the energy transfer can affect the structure of the solder itself leading to bonding within the solder and an enhancement of the strength of the solder and hence the join.

Drops of solder are typically used where the solder is a fluid solder, and are "painted" across the edges.

The solder can also be provided as a preformed solid strip.

The energy source is typically a laser.

A variety of tissue types can be joined using this method. The method is applicable to anastomoses of biological tubes including veins, arteries, lymphatics, nerves, vasa efferentia, fallopian tubes, bile ducts, tubes of the alimentary canal, the ureter, the urethra, tear ducts, bronchi and any other such bodily tubes as well as to repairs of incisions or tears of biological organs such as kidneys, liver or spleen, or of biological surfaces such as the peritoneum and skin. It will therefore be understood that the method can be used in a variety of join situations including the joining of cylindrical anastomoses and the closure of linear defects such as incisions.

Where the tissue repair is with respect to nerve tissue or other tissue tubes where the tube contents need to be protected from damage, it is especially important that the weld should not be concentrated on the edges being joined as this can damage extruded tissue. Rather, the weld should be distributed across the planar or tubular surface in which the discontinuity lies.

Where the tissue to be repaired is an essentially hollow body tube such as a blood vessel, the repair can additionally comprise the insertion of a thin-walled hollow cylinder of solder inside the tube under repair so that the cylinder spans the severed portions of the tube. Typically, while the severed tube and cylinder assembly is held together, energy from the energy source is directed through the tube wall to bond the cylinder to the tube ends. The cylinder may incorporate a dye, as hereinafter described, to attract energy to the cylinder for more efficient welding. The repair is completed by the application of at least one strip or drop of solder across the edges on the outer surface and treating the applied solder as described above.

Where the repair is with respect to tissue surfaces such as peritoneum, it will be understood that it is less important to avoid concentration of welding on the edges.

The method can also be modified for the repair of other discontinuities in tissue surfaces such as holes, resulting from accident or surgery. In this form of the invention the solder may be spread or pre-cut to conform to the shape of the repair site, and the edges of the repair site may not need to be aligned or abutted for the repair to be effected.

A typical nerve repair using the method of the invention is one in which the edges are ends of a cut peripheral nerve fascicle that are to be joined together or an end of a nerve fascicle and the fascicle of substitute nerve graft material. This latter situation is particularly applicable where nerve repair is required but a section of the nerve under repair has been severely damaged or is unavailable, so that the available ends of the fascicle are too remote from each other to be directly joined. The actual nature of the damage sustained by the nerve and whether the repair is a primary or secondary repair are factors affecting recovery but in any case the edges of nerve fascicles to be joined are cleanly cut at right angles prior to joining.

Application of the solder as a strip or strips, with space between for natural co-aptation of the surfaces themselves permits the nerve under repair to revascularise. Circumferential welding, by comparison, can inhibit the body's natural healing process and so slow down blood capillary access needed for the area of repair. Laser soldering and suturing techniques ultimately rely on the body regenerating connective tissue to hold the nerve together after either solder or suture connections break down and are replaced by the healing process. The present inventors have shown in vivo experiments that successful regeneration can be achieved by the methods of the present invention without restriction on surrounding tissue movement after the operation. In the case of nerve repair operation on human patients it is routine to initially restrict the movements of the joints of the operated limbs to assist in reducing tension across the repair site.

Typical biodegradable, biological solders useful in the method of the invention include protein solders.

It is envisaged that other naturally occurring biomolecules could be used as alternatives. Further analogues of biological, biodegradable polypeptides could be used. Analogues of biological, biodegradable polypeptides useful in the invention include synthetic polypeptides and other molecules capable of forming a viscous "glue" that does not react adversely within the tissue undergoing repair.

The protein solder may be a solid or a fluid solder composition.

Fluid protein solder compositions useful in strip welding typically comprise between 100 and 120 mass % of protein relative to water. Preferably, fluid protein solders comprise between 100 and 110 mass % protein relative to water.

The fluid solder strip is typically 50 to 200 μm in thickness. Its length is selected to suit the join to be formed but typically is of the order of 2 to 3 mm in length. It is typically painted across the join.

Solid protein solder compositions useful in strip welding typically comprise between 120 and 230 mass % protein relative to water. Preferably the strip comprises 170 to 230 mass % protein and more preferably about 210 mass %.

It will be understood that different proteins will have different degrees of solubility in water or appropriate solutions which in turn will affect the optimum concentration of protein in the composition for different protein solders. Appropriate ranges for particular proteins in both solid and fluid solders can be determined based on the known properties of the proteins.

Typically, the solid protein solder composition is provided as a preformed strip. Solid solder strips are easier to manipulate than fluid solders. Under the moist conditions inherent in surgery fluid solders may run making it difficult to laser denature the solder before it has spread. The solid solder strips can have a paste like or more rigid consistency. They are typically placed across the join with microforceps. In one form of the invention, it is envisaged that the solder strips will be substantially rectangular in shape. However, different shape strips may be required in different repair situations. It may also be desirable to provide a plurality of strips joined together for efficient repair of a large or a substantial number of repair sites.

The protein solder may comprise a single protein of which albumin is a typical example or alternatively the solder may comprise more than one protein.

Albumin has desirable qualities for solid solder strip formation since it has a high proportion of β sheet structure which gives rigidity to the strips. Fibrin is another example of a protein with significant β sheet structure. Incorporation of α helical protein in the solder can assist in making the strips more malleable and thus retain a flatter profile which is particularly well suited for joining nerve ends. An example of a suitable proportion of α helical protein is between 1 and 10% by weight of the protein used. About 5% is a preferred amount. Collagen, tropoelastin and elastin are examples of suitable a helical proteins.

Protein used in the solder is selected to minimise the risk of adverse host reactions and should therefore preferably be an autologous protein for the host or a foreign protein of low antigenicity.

The proteins may be obtained from any suitable source. Recombinantly or synthetically produced proteins as well as purified naturally occurring proteins may be used.

Preferably, when the solder is to be used with a laser which produces energy at a suitable wavelength the composition includes a substance, such as a dye, which absorbs energy at the wavelength produced by the laser with which the solder is to be used. It is preferable to choose the combination such that the dye or other substance absorbs the energy transmitted by the laser efficiently but the underlying tissue to be joined absorbs the transmitted energy poorly. The dye or other substance assists in making the welding specific to the solder used which in turn assists in minimising accidental tissue heating damage to the underlying tissue.

The process of bonding, where protein solders are used, relies on protein molecules being available for cross-linking. This occurs when the protein molecules are unfolded. Upon laser irradiation of, for instance, an albumin and indocyanine green containing solder at a nerve tissue join, albumin molecules are heated through energy transfer from the indocyanine green molecules, allowing them to unfold and bond between themselves and to neighbouring tissue surface such as the fascicle membrane.

Dyes which contrast with the tissues being repaired can also be useful in making the solder easier to see. An example of a dye with this property is indocyanine green.

When the laser used is a $CO_2$ laser, a dye will not assist the energy transfer, as the energy transfer is by water absorption.

The energy provided by the energy source should be sufficient to bond the solder to form the weld while minimising damage to the underlying tissue. The temperature required to denature a protein solder is typically at least 50° C. and may exceed 100° C. A preferred range is 50° to 90° C. A particularly preferred range is 80° to 90° C.

The time of treatment for each join to be effected can vary depending on such factors as ambient conditions, altitude, and of course the nature of the tissue to be joined. The duration of treatment is typically short. A 30 second passage for laser treatment of a 0.4 mg strip is an example of the time involved although it will be understood that shorter or longer treatment times could be required. It will be understood that solid solder takes longer to denature than fluid solder.

In a second aspect the present invention provides a protein solder composition comprising protein and a suitable solvent for the protein. Water is typically used as the solvent for water soluble proteins.

In a third aspect the present invention provides a kit for use in joining tissues comprising, in a preferably sterile pack, a plurality of protein solder strips and/or shapes of the second aspect of the invention. Preferably a plurality of strip lengths and/or shape sizes are included in the pack.

The kit preferably includes means for sterile manipulation of the strips. The kit also preferably includes means for measuring the strips.

The kit may also comprise an energy source such as a fibre coupled laser system.

BEST METHOD OF CARRYING OUT THE INVENTION

Figure 7:
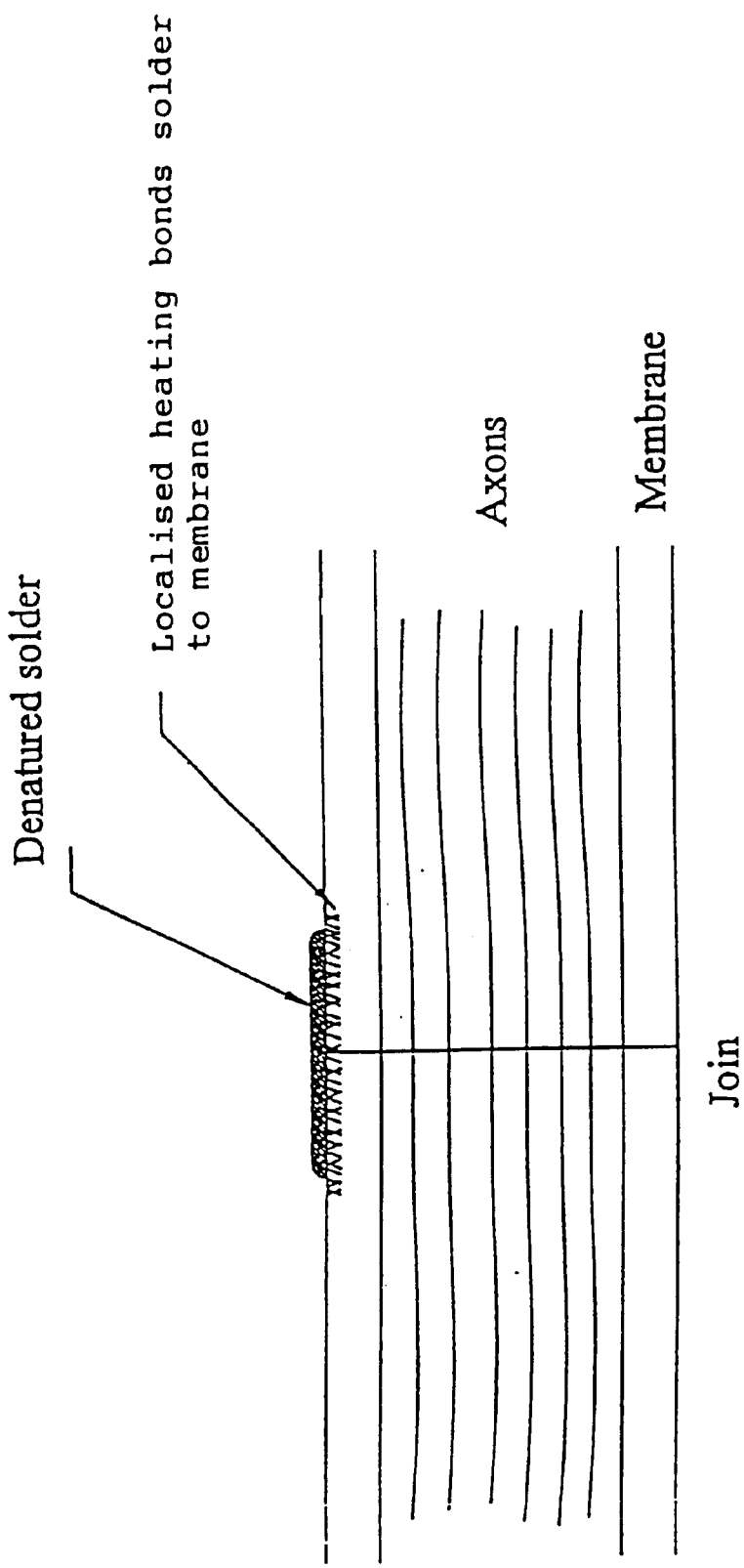
FIG. 7 shows in schematic form a cross-section of a repaired nerve fascicle.

Tissue repair is performed using a laser to activate a protein solder applied across the tissue edges to be joined. This solder denatures upon laser irradiation and bonds with itself and the neighbouring membrane to form the join. The procedure is shown schematically in FIGS. 3 and 7 for a repair to a nerve fascicle. The solder is applied in longitudinal strips across the join.

Nerve Repair

Repair to severed nerve tissues is effected by the placement of solder across the severed edges and exposure of the solder to laser as described above. In order to repair nerve tissue without damage to the contents of the nerve it is desirable to avoid concentrating the weld on the edges as extruded nerve contents may be damaged. Rather the weld should be distributed across the planar or tubular surface in which the discontinuity lies.

Hollow Body Tube Repair

Figure 6:
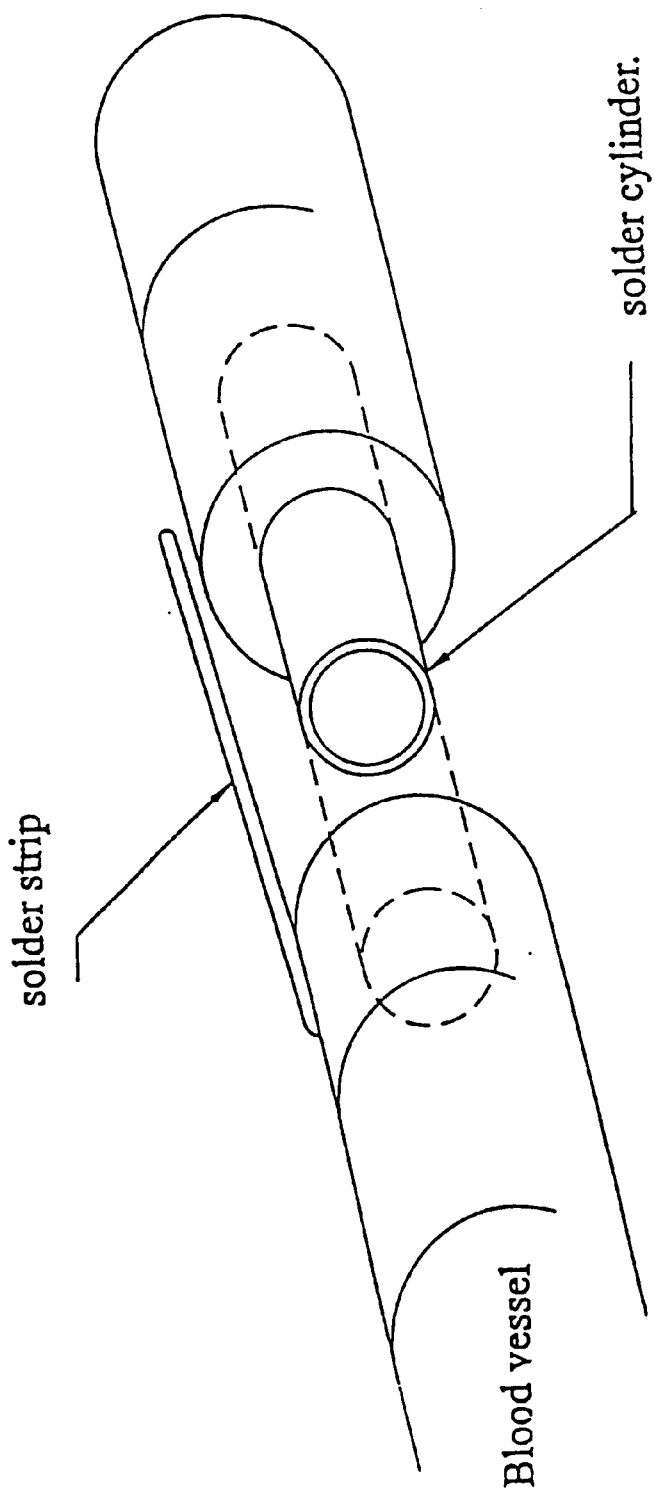
FIG. 6 shows in schematic form joining of a blood vessel using internal biodegradable solid solder cylinder and external solid solder strips.

When repairing hollow body tubes it is preferable to insert an internal cylinder of solder into the tube so that it lies between the discontinuity. The severed ends of the tube are placed over opposite ends of the solder cylinder. The arrangement is shown in FIG. 6. Lasering can then be effected to cause bonding of the cylinder to the tube being joined while the arrangement is held in place. If there is a good fit between the tube and the cylinder this laser step may not be required. The join is completed by the addition of external solder as for nerve repairs.

Tissue Surface Repairs

Surfaces such as peritoneum are planes of tissue in which joins without sutures can be achieved by the application of solder across the discontinuities to be joined and welding as described above. In this case it is less important to avoid concentration of welding on the edges.

Laser and Solder System Suited to Nerve Fasicular Repair

To denature the protein solder, a GaAs/GaAlAs laser diode with a nominal power of 250 mW (Spectra Diode Labs, San Jose, Calif.) is used. The laser light is coupled into a 100 µm diameter core optical fibre which is hand held in a fibre chuck. The diode is operated in continuous mode at 75 mW during the laser soldering. Because this laser is Class 3b, and is not eye safe, protective glasses must be worn at all times when using this laser.

A suitable protein solder is a mixture of water, albumin and indocyanine green (ICG) dye (Becton Dickinson, Mo.). Indocyanine green has a maximum absorption coefficient at a wavelength of 805 nm of $2 \times 10^5$ $M^{-1}$ $cm^{-1}$. The percentages of albumin and dye compared to the water were 110% and 0.6% respectively for fluid solder. 210% albumen was used in preparing solder strips. It is notable that ICG dye appears to preferentially bind with the albumin ensuring that heat is efficiently transferred to denature the protein solder.

Laser Soldering Technique

When conducting the surgery an operating microscope or some form of magnification is preferable. For a laser solder repair of a tubular join a section of thin gauze material is placed under the join to assist in a rotation technique. The tissue edges are prepared in accordance with standard techniques for the tissue type and geometry of the repair.

Using micro forceps the edges are aligned and butted together. A 2 mm long stripe of fluid solder is "painted" longitudinally across the junction of the edges using a 30 gauge needle freshly coated in the solder. Alternatively a strip solder is laid across the join using microforceps. The solid strip repair method is simpler. A solid strip is held in special microforceps and placed across the junction parallel to the length of the structures to be joined. The laser output is then directed at the solid strip and the solid solder changes colour signalling denaturation which causes it to adhere to the underlying tissue membrane. The process is repeated with further strips to ensure a strong union of surface.

The diode laser output from the 100 µm optical fibre is then used in a 30 second continuous pass to denature solid solder into a strip weld. At a diode output power of 75 mW, the solid solder strip turns brown on the surface and opaque underneath from the single pass, signalling denaturation. When using fluid solder denaturation occurs more quickly. A two second laser pass can be sufficient to denature the fluid solder. Generally a second layer of fluid solder is applied to the strip in order to increase the strength of the weld and the two second laser pass is repeated. The gauze under the join is then used with the micro-forceps to rotate the join so that other strips can be applied.

Preparation of Fluid Protein Solder
Composition
Albumin (fraction V powder from Sigma, St. Louis, Mo.) at least 100% to 110% by weight compared to water.
Indocyanine Green (Becton Dickinson, Mo.) approximately 0.6% by weight compared to water.
Water (injection grade)

Procedure

A solution of ICG in water was prepared in a minitube. The albumin was added to the tube. The albumin and solution were mixed using a vortex mixer. This causes the protein structure to change leading to linkage of protein molecules to each other rather than to water molecules.

Preparation of Solid Protein Solder
Composition
Albumin (fraction V powder from Sigma, St. Louis, Mo.) 210% by weight compared to water
Indocyanine Green (Becton Dickinson, Mo.) approximately 0.6% by weight compared to water
Water (injection grade)

Procedure

The ICG was dissolved in the water and the albumin was added to this solution in a minitube. This combination was mixed using a vortex mixer and a needle. The combination was mixed (for approximately 3 minutes) until it became a homogenous, malleable, green paste. The phase of the mixture changed under this mixing technique to provide an almost solid composition with mainly protein to protein linkages rather than protein to water linkages. The system is no longer a solution at this stage. The protein paste was malleable and could be cut into strips for up to about 30 minutes after mixing. After this time the paste hardened due to dehydration and became too hard to cut.

The resulting strips were between 50 and 100 µm in thickness, about 0.6 mm wide and 1.5 to 3.5 mm long. It will be understood that where the strips are used in mending nerve fascicles that the desired width and length are dictated by fascicle dimensions. The width, thickness and length mentioned here are those suitable for use with a rat tibial nerve which has a diameter of 0.2 to 0.8 mm. The ratio of strip width to nerve circumference is typically:

Width ~1/5 circumference

EXAMPLE 1

A 100 µm core optical fibre-coupled 75 mW diode laser operating at a wavelength of 800 nm has been used in conjunction with a protein solder to stripe weld severed rat tibial nerves, reducing the long operating time required for microsurgical nerve repair. Welding is produced by selective laser denaturation of the protein based solder which contains the dye indocyanine green. Operating time for laser soldering was 10+/−5 min. (n=24) compared to 23+/−9 min. (n=13) for microsuturing. The laser solder technique resulted in patent welds with a tensile strength of 15+/−5 g, while microsutured nerves had a tensile strength of 40+/−10 g. Histopathology of the laser soldered nerves, conducted immediately after surgery, displayed solder adhesion to the outer membrane with minimal damage to the inner axons of the nerves. An in vivo study, with a total of fifty-seven adult male wistar rats, compared laser solder repaired tibial nerves to conventional microsuture repair. Twenty-four laser soldered nerves and thirteen sutured nerves were characterised at three months and showed successful regeneration with average Compound Muscle Action Potentials (CMAP) of 2.4+/−0.7 mV and 2.7+/−0.8 mV respectively. Histopathology of the in vivo study, confirmed the comparable regeneration of axons in laser and suture operated nerves. A faster, less damaging and long lasting laser based anastomotic technique is presented.

Materials and Methods

1. Animals

A total of fifty-seven young adult male Wistar rats weighing between 400 and 550 g at the outset were used in this study. Thirty-four rats received laser solder repair and the remaining twenty-three received standard microsuture repair as detailed below. Five rats of each repair method were used for tensile strength measurements and light microscopy immediately after surgery and the remaining thirty-seven rats were subjected to a study of functional recovery using electrophysiology and histopathology.

2. Laser Solder System

To denature the protein solder, a GaAs/GaAlAs laser diode with a nominal power of 250 mW (Spectra Diode Labs, San Jose, Calif.) was used. The laser light was coupled into a 100 µm diameter core optical fibre which was hand held in a fibre chuck. The diode laser was mounted on a heat sink, and the diode current and temperature were controlled by a SDL-800 diode driver. The diode was operated in continuous mode at 75 mW during the laser soldering, corresponding to a maximum power density of 955 W/cm at the tissue. The laser output power was measured with a Scientech (Boulder, Colo.) power meter. Because this laser is Class 3b, and is not eye safe, protective glasses were worn at all times when using this laser.

The solder used in this study was an albumin based protein mixture, also containing indocyanine green (ICG) dye (Becton Dickinson, Mo.). Indocyanine green has a maximum absorption coefficient at a wavelength of 805 nm of $2 \times 10^5$ $M^{-1}$ $cm^{-1}$. It is notable that this dye appears to preferentially bind with the proteins ensuring that heat is efficiently transferred to denature the protein solder.

3. Surgery

Anaesthesia was maintained during surgery using a mixture containing Fluothane (4% during induction, 2% thereafter) in $O_2$ (1 L/min). Using a OPMI 7 operating microscope (Zeiss, West Germany) the sciatic nerve of the left leg was exposed at the sciatic notch so that the nerve branches could be distinguished. The tibial branch, just below the sciatic notch, was exposed from the surrounding subcutaneous tissue for a length of 1 cm. For a laser solder repair, a section of thin gauze material was placed under the tibial nerve to assist in rotation of the nerve, and for the suture repair, a section of plastic was placed under the nerve to allow easier suturing. The tibial nerve was then severed with serrated micro-scissors and left for 3 minutes for the normal extrusion of axoplasm to occur. This was then trimmed with the serrated micro-scissors as required, after which the nerve was repaired with either four laser solder strips or four 10-0 perineurial sutures.

Figure 1:
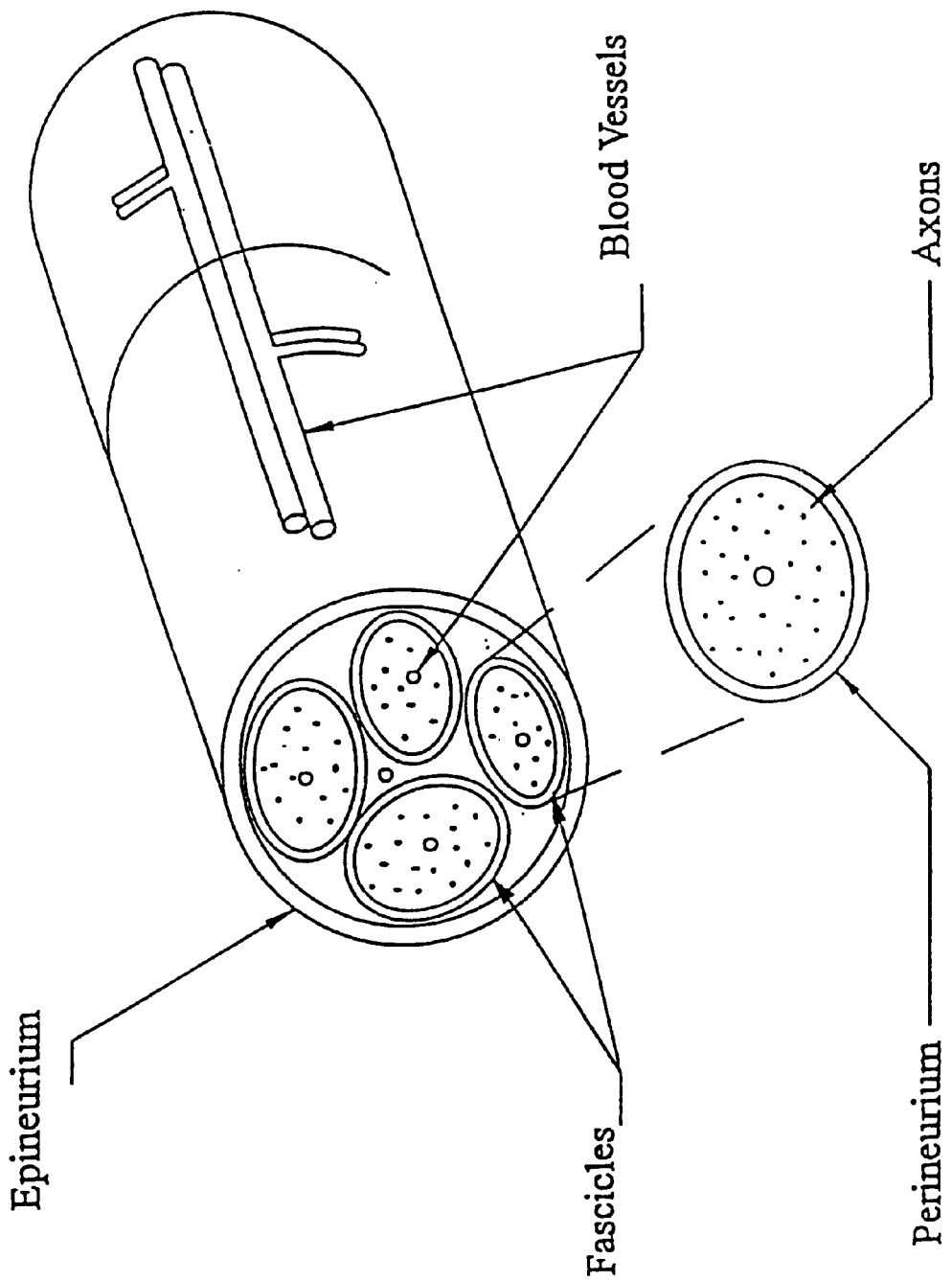
FIG. 1 shows the structure of a peripheral nerve in schematic form.
Figure 2:
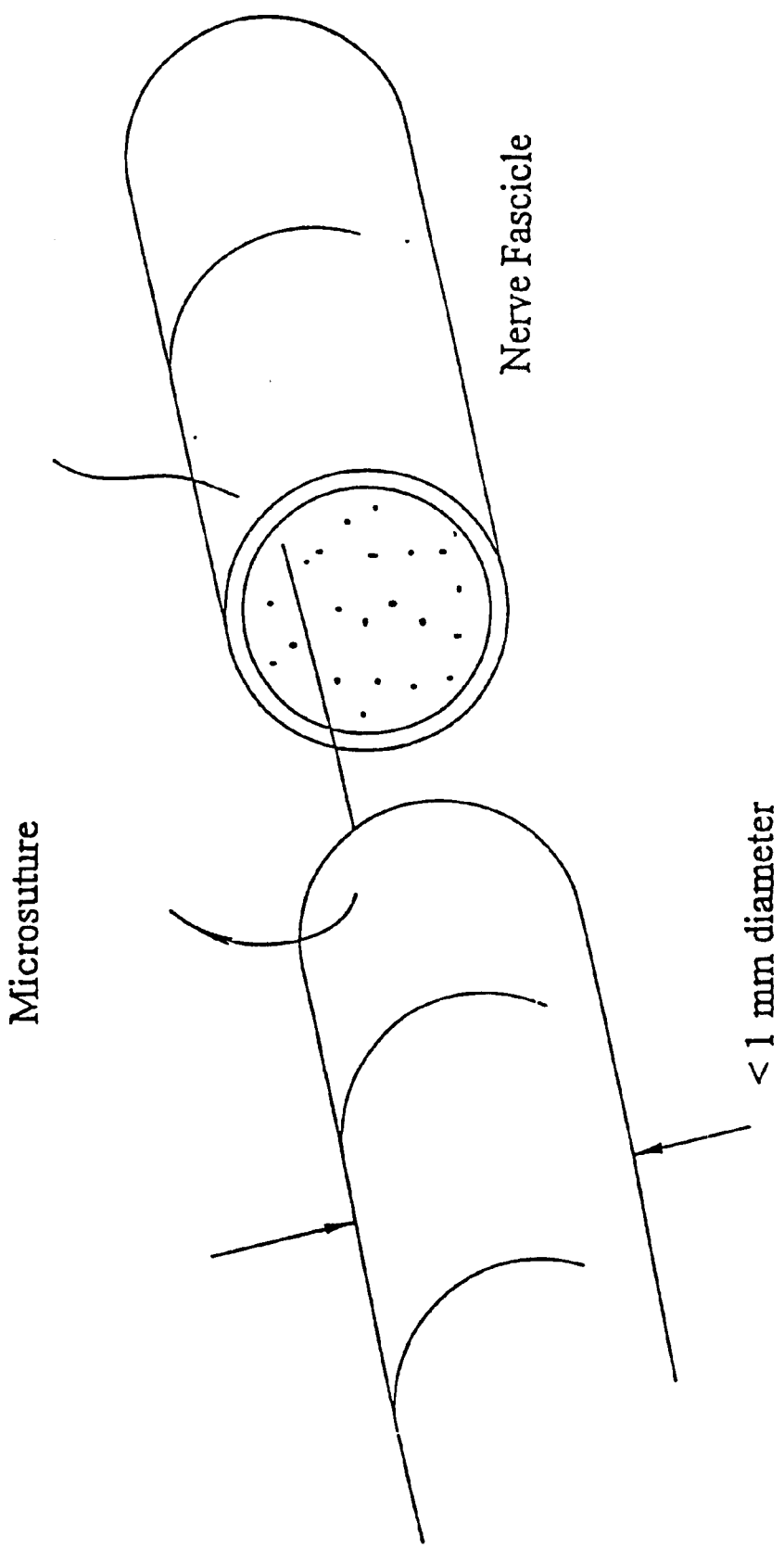
FIG. 2 shows the joining of a peripheral nerve by prior art microsuturing techniques.
Figure 3A:
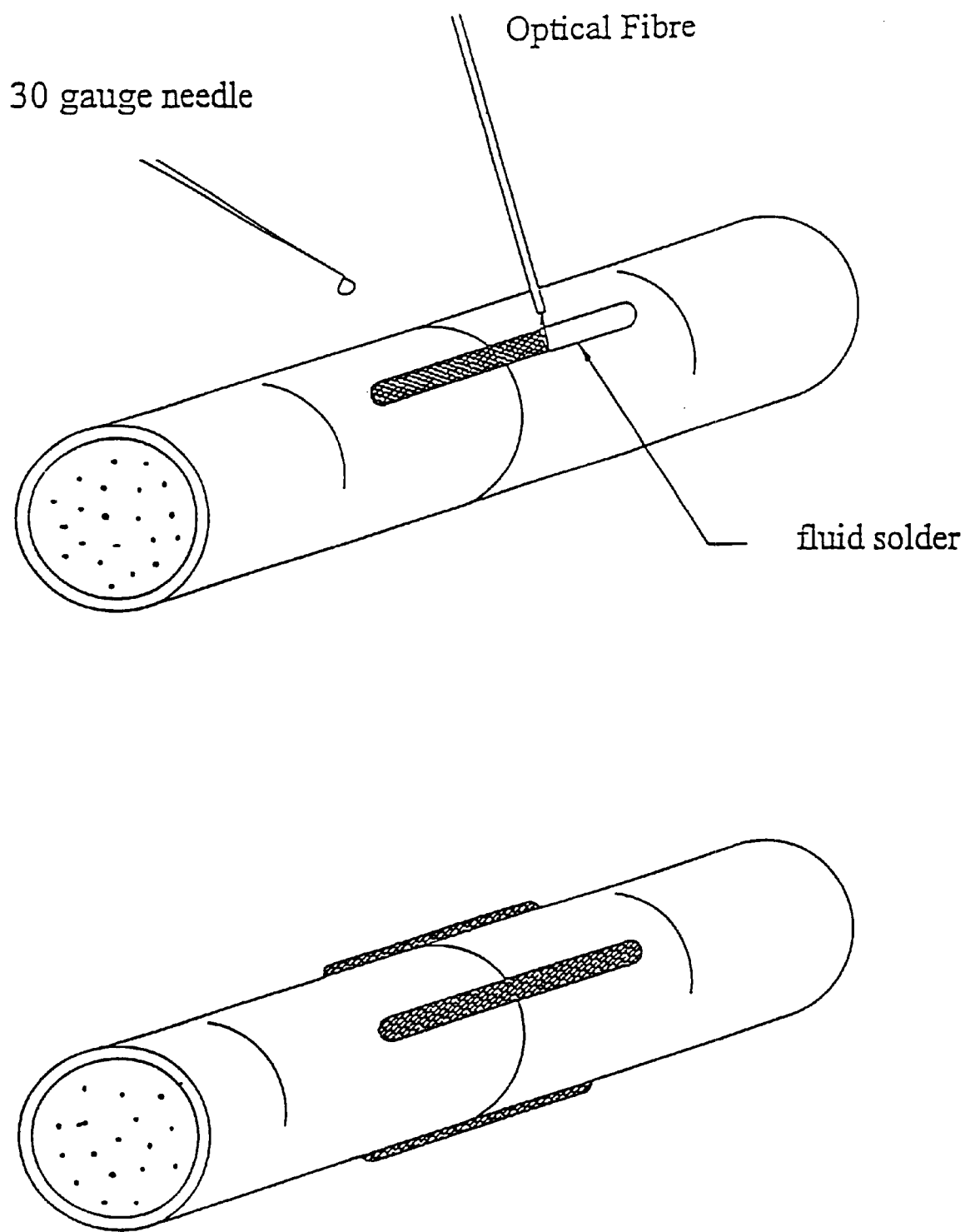
FIGS. 3a) and b) shows in schematic form joining of a nerve fascicle with a) fluid solder and b) solid strips.
Figure 3B:
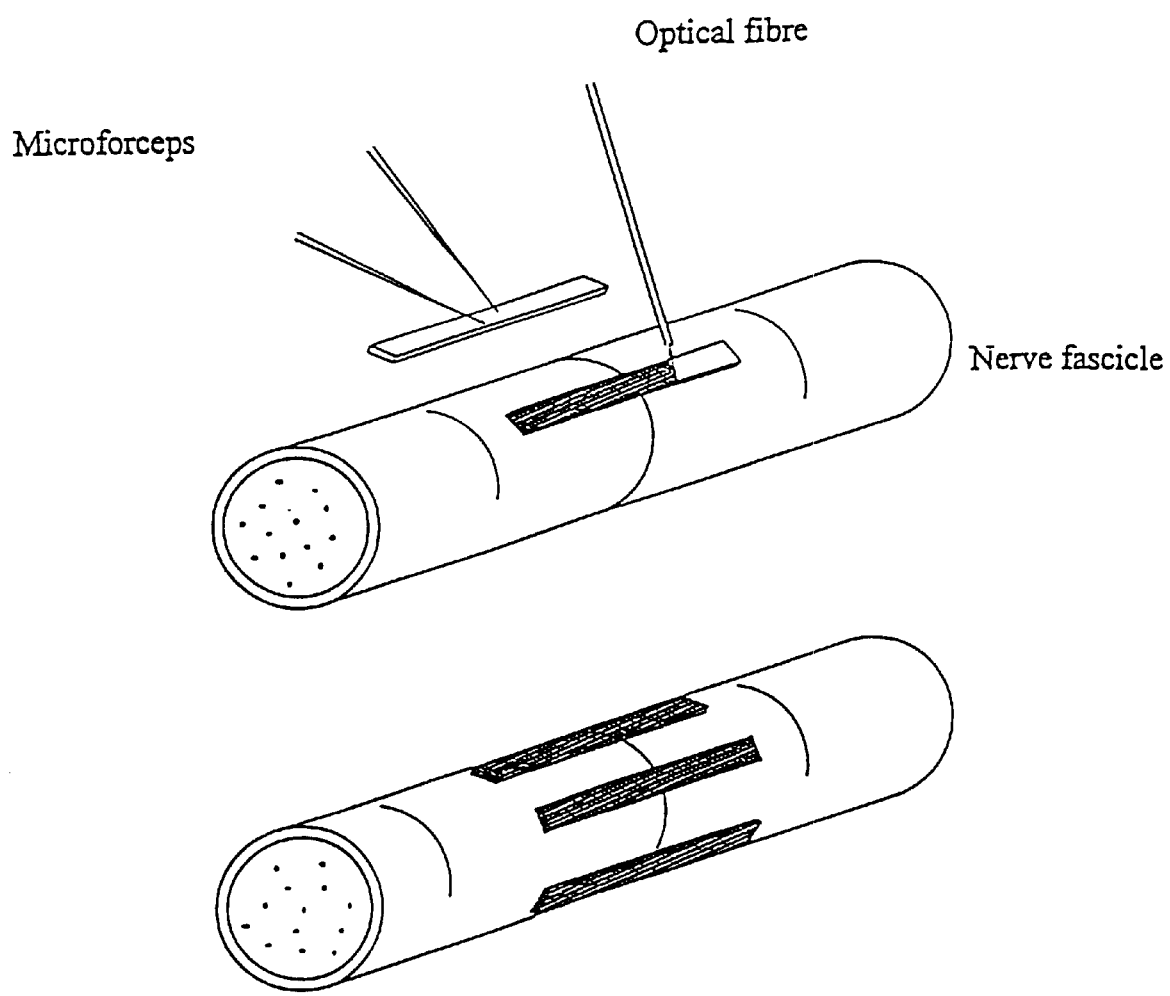
Figure 4B:
FIG. 4B shows the repair site of a 0.3 mm diameter tibial nerve immediately after microsuturing.
Figure 4A:
FIG. 4A shows the repair site of a 0.3 mm diameter tibial nerve immediately after diode laser strip welding.

The laser solder method involved aligning both stumps of the severed nerve with micro-forceps then a 2 mm long strip of solder was "painted" longitudinally across the junction of the severed ends using a 30 gauge needle freshly coated in the solder (FIG. 3a). The diode laser output from the 100 $\mu$m optical fibre was then used in a continuous two second pass to denature the solder into a strip weld. At a diode output power of 75 mW, the solder was observed to turn brown on the surface and opaque underneath from the single pass, signalling denaturation. A second layer of solder was applied to the strip and the two second laser pass was repeated. The gauze under the nerve was then used with the micro-forceps to rotate the nerve so that three other two layered stripes could be applied, each approximately 90° apart.

Figure 9:
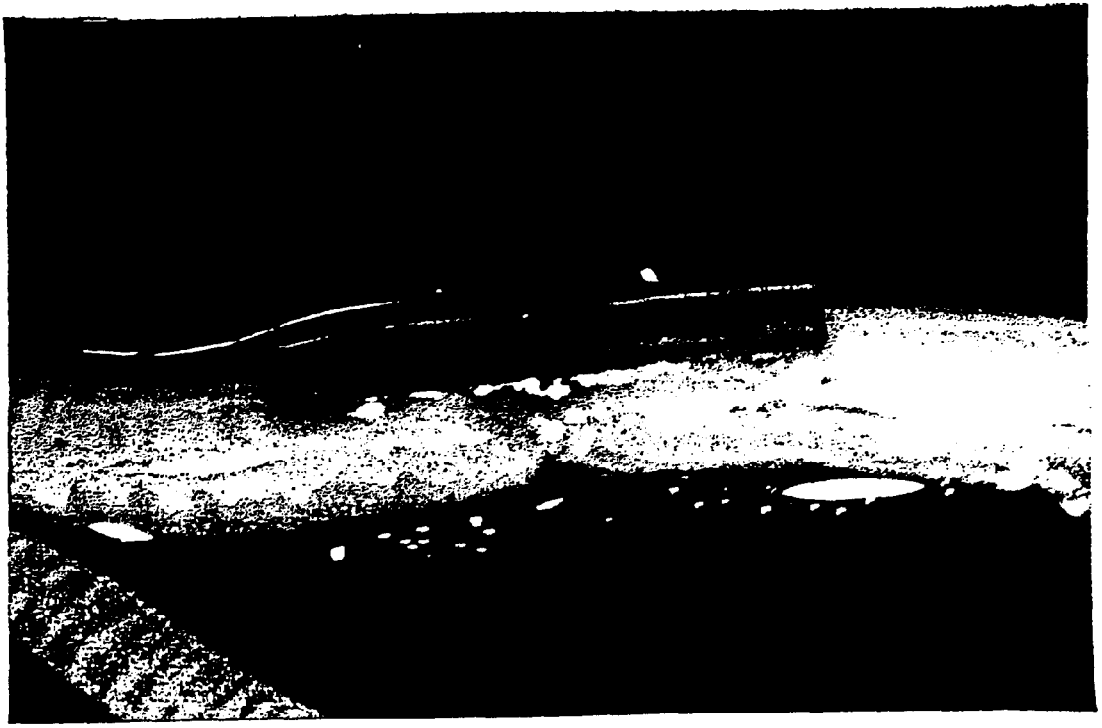
FIG. 9 shows a solid solder strip positioned upon a severed rat tibial nerve just prior to laser welding.

Seven rats were operated with a more advanced version of the organic solder, which is still an albumin based protein mixture but it has the advantage to be dehydratated and cut into solid rectangular strips (FIG. 9). The average surface area of the solder strips was 1.5+/−0.5 $mm^2$ and the thickness was 0.15+/−0.01 mm. Four strips were positioned along the tibial anastomized nerve and then radiated with the same procedure adopted for the fluid solder. The solid strip was fused with the perineurium of the tibial nerve by the laser radiation, joining the extremites of the sectioned nerve.

For all operation the time of anastomosis was recorded and a photographic record was taken for later reference. The animals were placed in their cages with no restriction of movement for 3 months.

4. Immediate Measurement of Tensile Strength and Histopathology

Figure 8:
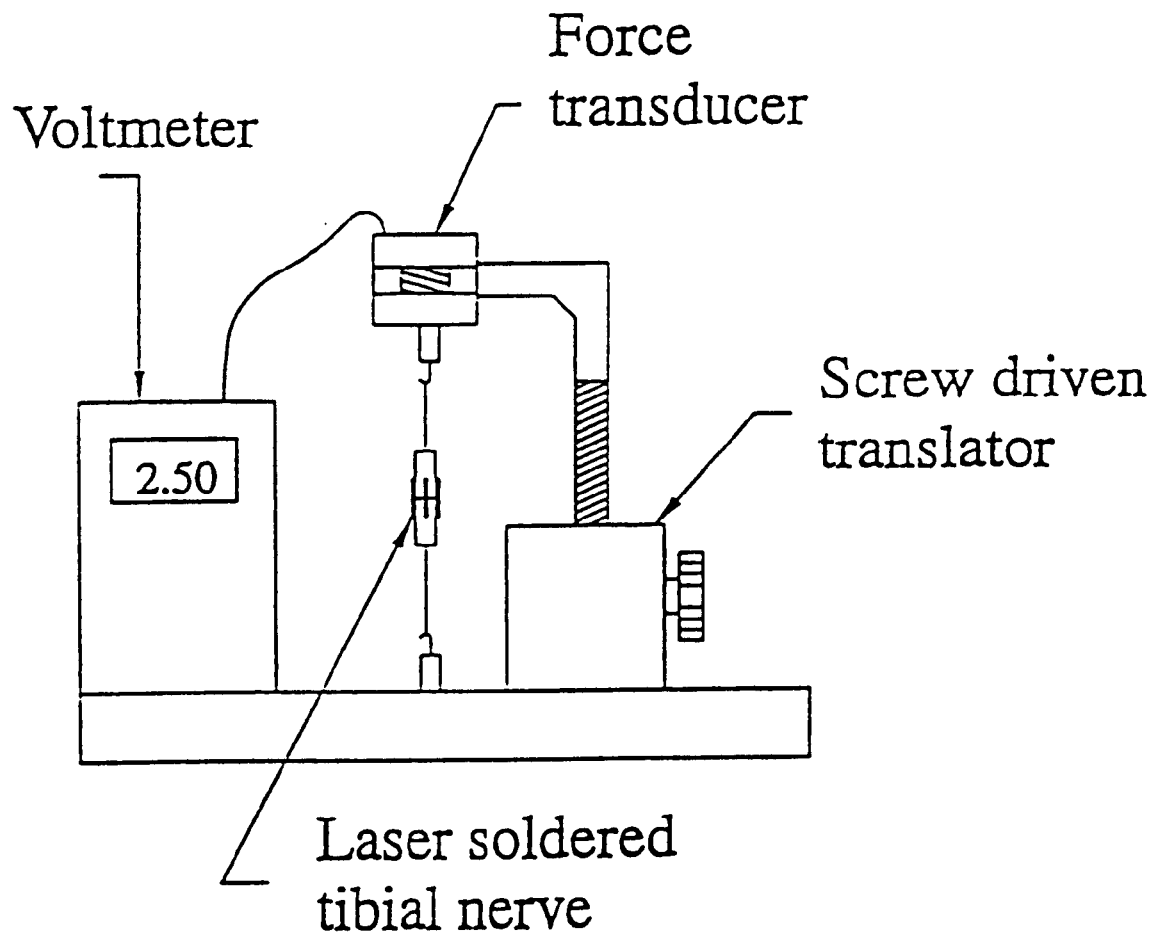
FIG. 8 shows the method used for measuring tensile strength of repaired nerves.

In ten of the operated rats, the 1 cm long section of the laser and suture repaired nerves was harvested immediately for tensile strength measurements. Fine silk was tied to each end of the tibial nerve. One end was then attached to a calibrated force transducer (FT30C, Grass Instruments, Quincy, Mass.) and the other to a screw driven translator (FIG. 8) As the screw was turned the translator would stretch the nerve in a slow and steady manner. The applied tension was observed on an oscilloscope connected to the output of the force transducer. Tension was applied until the nerve separated, and the breaking force was recorded. The nerves were kept moist, as upon drying, the tensile strength can be increased.

For light microscopy the anastomosis site of the tibial nerves were fixed in 5% formalin, alcohol dehydrated, imbedded in paraffin, longitudinally sectioned and stained with either Masson's trichrome or Giemsa.

5. Functional Assessment: Histopathology and Electrophysiology

Three months post operatively the rats were reanaesthetised using the method described in section 3. The site was exposed and the anastomosis of the tibial nerve observed. The two other branches of the sciatic nerve, the peroneal and sural nerves were then severed so that only the tibial nerve branch of the sciatic nerve could conduct electrical stimulation of the sciatic nerve to the muscles of the hind foot. Two days later the rats were positioned on their side and insulated from the table by a folded surgical drape. An infrared lamp was used to maintain their rectal temperature above 36° C.

A clinical electromyograph (Cadwell Sierra EMG/EP), was used for stimulation and recording. Two 25 gauge stimulating electrodes were placed 10 mm apart on each side of the sciatic nerve above the sciatic notch, near the hip. The nerve was activated using rectangular pulses (0.1 to 0.3 ms; 0 to 30 mA; 1 Hz). Compound muscle action potentials (CMAPs) were recorded from the plantar muscles of the foot in response to supramaximal stimulation of the sciatic nerve. A set of three recording electrodes were used. A 25 gauge ground electrode was inserted subcutaneously between the stimulating and recording electrodes [1,2]. A 30 gauge reference electrode was inserted into the heel pad and a 30 gauge recording electrode was inserted into the plantar muscles of the foot. The CMAPs were recorded and processed to determine their negative wave peak value.

Histopathology of the sutured and laser soldered nerves, was conducted after the Electrophysiology test with the same procedure as adopted in section 4.

Results

At the completion of surgery all anastomoses were successful. The operating procedure was found to be easier for laser soldering than for microsuturing. This resulted in the shorter operating times for laser solder repairs {10±5 min (n=24)} than {23±9 min (n=13)} for microsuture repairs. The tensile strength of five laser solder repaired nerves immediately after the operation was 15±5 g and the tensile strength of the microsutured nerves, 40±10 g.

Histopathological examination of the anastomosis sites immediately after surgery demonstrated that the albumin and ICG dye based laser solder does bond well with the outer membrane of the nerve, the perineurium, while the inner axons remain unheated. In FIG. 10a, a tibial nerve fascicle weld produced by the diode laser and albumin/ICG dye solder is shown in section. Both the protein solder and the perineurium have denatured forming the bond. On the lower side of the bond, the axoplasm has its normal wavy structure. Note that since heating is concentrated at the dye, only denaturation of the solder and adjacent perineurium occurs.

Figure 5B:
FIG. 5b shows a rat sciatic nerve joined by microsuturing using 10-0 nylon. Localised perineural and axonal damage occurs.
Figure 5A:
FIG. 5a shows a rat tibial nerve welded by the laser solder methods of the present invention. The solder and the membrane are denatured but no significant change to the axons has occurred (x100 Giemsa).

One of the promising aspects of laser anastomosis is the potential for reduced damage to the axoplasm by removing the need for sutures. A section showing the effect of microsuturing nerve fascicles using 10/0-nylon is shown in FIG. 5b. This section stained with Giemsa, displays axon extrusion at the join, as well as localised perineurial and axonal damage due to the suture.

Histopathology at 3 months shows regeneration of myelinated axons in laser nerve repairs (FIG. 10a), with no discontinuity of either the fibers and their sheaths, or the fibrous perineurium. No evidence is seen of inflammation or myelin phagocytosis. Full restoration, as assessed by light microscopy, of the histologic integrity of the tibial nerve has been achieved by the laser weld.

Figure 10B:
FIG. 10b shows fibrous tissue around a suture in a sutured nerve that has regenerated for 3 months.
Figure 10A:
FIG. 10a shows regeneration of myelinated axons in a laser nerve repair that has regenerated for 3 months.

The sutured nerves also show successfull anastomosis with myelinated axon regeneration, however, it is still evident that the nylon thread is surrounded by fibrous tissue, which creates an obstacle to the directionality of the regenerated axons (FIG. 10b).

Figure 11:
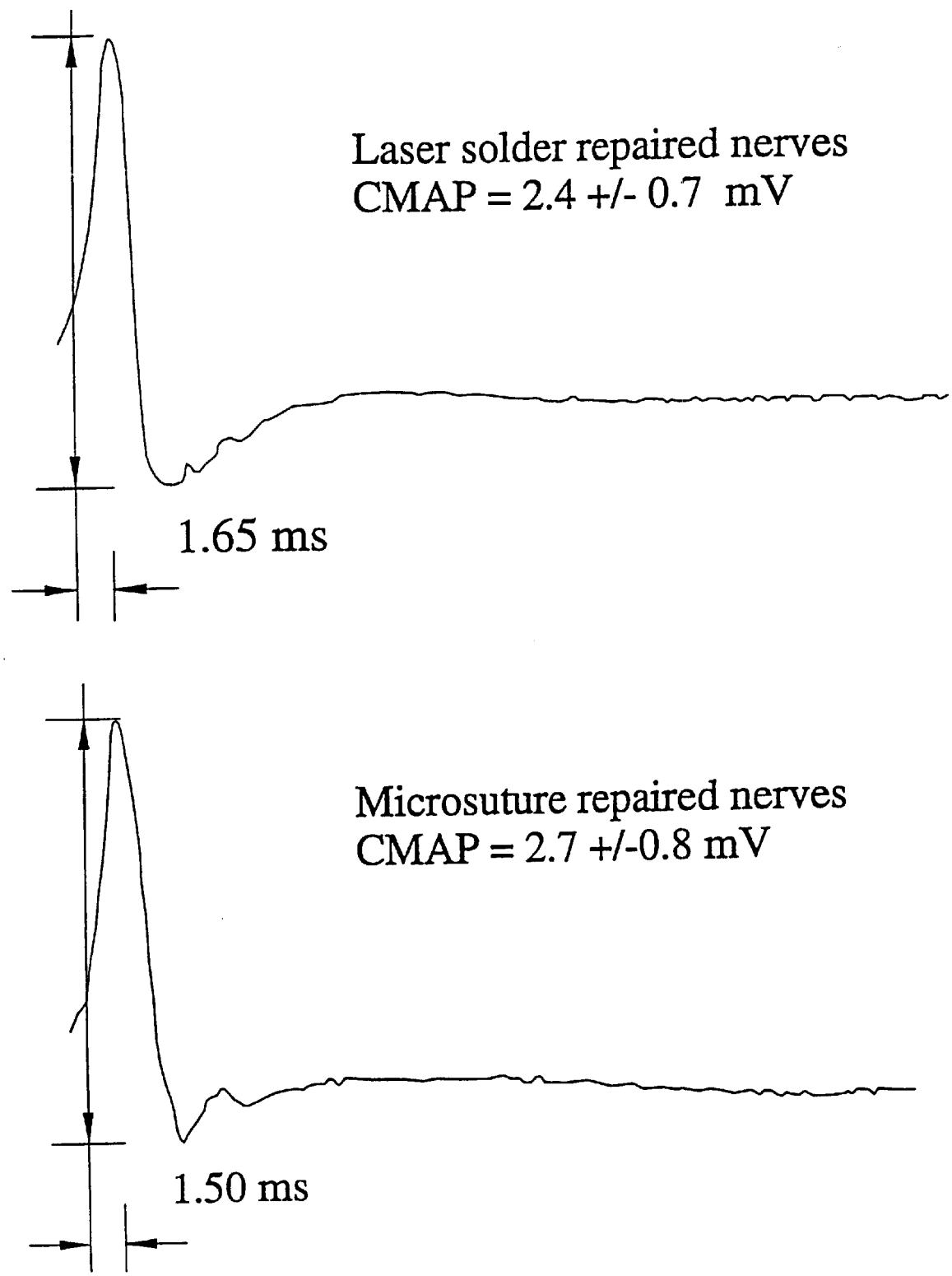
FIG. 11 shows muscle action potential results for repaired nerves.

The electrophysiological measurements of the in vivo study were performed on twenty-four laser solder repaired rats and thirteen microsuture repaired rats having three months recovery. Of this group all twenty-four laser solder anastomoses were patent as were the thirteen microsuture anastomoses. The average amplitude of the muscle action potentials, resulting from supramaximal stimulation of the nerve above the repair site was 2.4+/−0.7 mV for the twenty-four laser soldered tibial nerves and 2.7+/−0.8 mV for the thirteen microsutured nerves. The normal muscle action potential produced by stimulating the tibial nerve supramaximally was recorded at 8.7±3 mV from ten rats (FIG. 11).

Discussion

Clinically, when a major peripheral nerve is severed, forty or more fascicles may need to be individually rejoined. With three or four microsutures per fascicle, suturing tends to be prolonged, as it must be meticulous. In a nerve graft, where two anastomoses are needed, the suturing time is doubled. We have sought a suitable method of nerve anastomosis that could at least duplicate the end result but was significantly faster than the present hand sewing microsuture technique. A bonus of the described laser soldering method was the demonstrated lack of change to the axonal components beneath the denatured perineurial layer seen immediately after surgery. Three months later comparable regeneration was demonstrated by electrophysiological nerve conduction studies.

Industrial Applicability

The present invention has application in the field of surgery where it is of application in joining together tissue edges, in end to end, side to end and side to side applications.

REFERENCES

1) R. Malik, S. Ho and D. B. Church: A new method for recording and analysing evoked motor potential from dogs. *Journal of Small Animal Practice* (1989) 30, 13–19.
2) R. Malik, S. Ho: Motor nerve conduction parameters in the cat. *Journal of Small Animal Practice* (1989) 30, 396–400.
3) Laser activated protein bands for peripheral nerve repair. A Lauto, R Trickett, R Malik, J Dawes, E Owen. European Biomedical Optics Week—BIOS Europe 195 12–16 September 1995 (Proceeding in Press)

What is claimed is:

1. A method for joining tissue comprising:
   aligning and abutting edges of the tissue to be joined;
   applying a biodegradable, biological solder or an analogue thereof across the edges as one or more transverse strips; and
   exposing the solder to an energy source under conditions which provide transfer of energy from the source to the solder to cause the solder to bond to the tissue surface adjacent the edges to provide a weld holding the edges together, wherein when more than one strip is applied, the strips are spaced apart to permit natural co-aptation of the join.

2. The method of claim 1 wherein the tissue is nerve tissue and the edges are ends of a peripheral nerve fascicle or a nerve fascicle and nerve graft material, and welding is-not effected along the line of discontinuity so as to protect nerve tissue from damage.

3. The method of claim 1 wherein the tissue is an anastomosis of a biological tube selected from the group consisting of veins, arteries, lymphatic, vasa efferentia, fallopian tubes, bile ducts, tubes of the alimentary canal, the ureter, the urethra, tear ducts and bronchi, and wherein a hollow cylinder of the solder is inserted into the biological tube between discontinuous edges of the anastomosis prior to the application of the one or more strips of the solder to the external surface of the biological tube.

4. The method according to claim 3 wherein the discontinuous edges are held in place while energy is applied to the cylinder within the tube to cause the cylinder to bond with the inner surface of the tube.

5. The method of claim 1 wherein the tissue is a repair of an incision or tear of a biological organ including kidneys, liver or spleen, or of a biological surface.

6. The method according to claim 1, further comprising applying a first strip of the solder and exposing said first strip to the energy source; applying a second strip close to the first strip and exposing said second strip to the energy source; and repeating said applying and exposing steps to provide a plurality of strip welds.

7. The method according to claim 1, wherein the biodegradable, biological solder is a protein solder.

8. The method of claim 7 wherein the protein solder is a solid or a fluid solder.

9. The method according to claim 1, wherein the energy source is a laser.

10. The method according to claim 1, wherein the solder incorporates a substance which efficiently absorbs the energy from the energy source compared to absorption of the energy by the tissue.

11. The method according to claim 10 wherein the substance is a dye.

12. The method according to claim 1, wherein the biological solder is a fluid protein solder composition comprising 100 to 120 parts by weight protein per 100 parts by weight of a suitable solvent.

13. The method according to claim 12, wherein the fluid protein solder composition comprises 100 to 110 parts by weight protein.

14. The method according to claim 12, wherein the protein solder composition further comprises a substance which efficiently absorbs energy from an energy source compared to absorption of the energy by the tissue.

15. The method according to claim 14, wherein the substance is a dye.

16. The method according to claim 12, wherein the protein is albumin.

17. The method according to claim 12, wherein the protein contains βsheet structure.

18. The method according claim 12, wherein the protein has between 1 and 10% by weight αhelical content.

19. The method according to claim 12, wherein the solvent is a water-containing solvent.

20. The method according to claim 12, wherein the solvent is water.

21. The method according to claim 1, wherein the biological solder is a substantially solid protein solder composition comprising 120 to 230 parts by weight protein per 100 parts by weight of a suitable solvent.

22. The method according to claim 21, wherein the protein solder composition comprises 170 to 230 parts by weight protein.

23. The method according to claim 22, wherein the protein solder composition comprises about 210 parts by weight protein.

24. The method according to claim 21, wherein the protein solder composition further comprises a substance which efficiently absorbs energy from an energy source compared to absorption of the energy by the tissue.

25. The method according to claim 24, wherein the substance is a dye.

26. The method according to claim 21, wherein the protein is albumin.

27. The method according to claim 21, wherein the protein contains βsheet structure.

28. The method according to claim 21, wherein the protein has between 1 and 10% by weight αhelical content.

29. The method according to claim 21, wherein the solvent is a water-containing solvent.

30. The method according to claim 21, wherein the solvent is water.

31. The method of claim 1, wherein the tissue is an anastornosis of a biological tube, and wherein a cylinder of the solder is inserted into the tube between the edges prior to the application of the one or more strips of the solder to the external surface of the biological tube.

32. A method for repairing a discontinuity in a tissue surface, comprising:

applying a biodegradable, biological solder or an analogue thereof to the discontinuity; and exposing the solder to an energy source under conditions which provide transfer of energy from the source to the solder to cause the solder to bond within itself and to the tissue surface to provide a weld holding the solder and tissues surrounding the discontinuity together;

wherein the biological solder is a fluid protein solder composition comprising 100 to 120 parts by weight protein per 100 parts by weight of a suitable solvent.

33. The method according to claim 32, wherein the biological solder further comprises a substance which efficiently absorbs energy from an energy source compared to absorption of the energy by the tissue.

34. The method according to claim 33, wherein the substance is a dye.

35. The method according to claim 32, wherein the protein is albumin.

36. The method according to claim 32, wherein the protein contains βsheet structure.

37. The method according to claim 32, wherein the protein has between 1% and 10% by weight αhelical content.

38. The method according to claim 32, wherein the solvent is a water-containing solvent.

39. The method according to claim 32, wherein the solvent is water.

40. A method for repairing a discontinuity in a tissue surface, comprising:

applying a biodegradable, biological solder or an analogue thereof to the discontinuity; and exposing the solder to an energy source under conditions which provide transfer of energy from the source to the solder to cause the solder to bond within itself and to the tissue surface to provide a weld holding the solder and tissues surrounding the discontinuity together;

wherein the biological solder is a substantially solid protein solder composition comprising 120 to 230 parts by weight protein per 100 parts by weight of a suitable solvent.

41. The method according to claim 40, wherein the protein solder composition comprises 170 to 230 parts by weight protein.

42. The method according to claim 40, wherein the biological solder further comprises a substance which efficiently absorbs energy from an energy source compared to absorption of the energy by the tissue.

43. The method according to claim 42, wherein the substance is a dye.

44. The method according to claim 40, wherein the protein is albumin.

45. The method according to claim 40, wherein the protein contains βsheet structure.

46. The method according to claim 40, wherein the protein has between 1% and 10% by weight αhelical content.

47. The method according to claim 40, wherein the solvent is a water containing solvent.

48. The method according to claim 40, wherein the solvent is water.

49. The method according to claim 40, wherein the biological solder is applied to the discontinuity as a preformed strip.

50. The method according to claim 48, wherein the preformed strip has a thickness in a range of between 50 and 100 μ.

* * * * *

UNITED STATES PATENT AND TRADEMARK OFFICE
CERTIFICATE OF CORRECTION

PATENT NO.      : 6,583,117 B2
DATED           : June 24, 2003
INVENTOR(S)     : C. Delacroix It is certified that error appears in the above-identified patent and that said Letters Patent is hereby corrected as shown below:

Column 5,
Line 2, replace "a" with -- α --.

Column 7,
Line 15, replace "albumen" with -- albumin --.

Column 12,
Line 15, replace "is-not" with -- is not --.

Column 13,
Line 37, insert -- biological -- before "tube".
Line 37, insert -- discontinuous -- before "edges".

Signed and Sealed this

Seventeenth Day of February, 2004

JON W. DUDAS
*Acting Director of the United States Patent and Trademark Office*